United States Patent [19]

Zirngibl et al.

[11] 4,330,545
[45] May 18, 1982

[54] HETEROCYCLIC IMIDAZOLYL VINYL ETHERS AND USE OF SAME AS FUNGICIDES OR BACTERICIDES

[75] Inventors: Ludwig Zirngibl, Zofingen; Johanna Fischer, Reiden; Kurt Thiele, Zofingen, all of Switzerland

[73] Assignee: Siegfried Aktiengesellschaft, Zofingen, Switzerland

[21] Appl. No.: 150,964

[22] Filed: May 19, 1980

Related U.S. Application Data

[63] Continuation-in-part of Ser. No. 970,312, Dec. 18, 1978, Pat. No. 4,210,656, and Ser. No. 970,330, Dec. 18, 1978, Pat. No. 4,210,657.

[30] Foreign Application Priority Data

Feb. 21, 1977 [DE]  Fed. Rep. of Germany ....... 2757113
Sep. 11, 1978 [DE]  Fed. Rep. of Germany ....... 2839388

[51] Int. Cl.³ .................... A01N 43/50; A01N 43/54; A01N 43/56; C07D 401/12; C07D 403/12; C07D 407/12; C07D 409/12
[52] U.S. Cl. .................................. 424/263; 542/405; 542/458; 542/466; 542/467; 544/239; 544/284; 544/316; 544/318; 544/319; 544/405; 546/153; 546/157; 546/278; 548/255; 548/256; 548/336; 424/250; 424/251; 424/258; 424/273 R; 424/273 P; 542/413
[58] Field of Search ..................... 542/405, 458, 413; 546/278, 153, 157; 548/336, 255, 265; 544/316, 318, 319, 239, 284, 405; 424/273 R, 273 P, 258, 263, 250, 251

[56] References Cited

U.S. PATENT DOCUMENTS

4,067,989  1/1978  Shephard et al. ................... 542/405
4,073,925  2/1978  Balasubramanyan et al. ..... 548/336
4,177,350  12/1979  Zirngibl et al. ...................... 546/278

*Primary Examiner*—Henry R. Jiles
*Assistant Examiner*—N. Harkaway
*Attorney, Agent, or Firm*—Burns, Doane, Swecker & Mathis

[57] ABSTRACT

Aryl-imidazol-1-yl vinyl ethers and their acid addition salts are disclosed, wherein the imidazolyl vinyl ether has the formula:

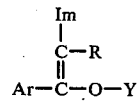

Ar in the formula represents a substituted or unsubstituted aryl or heterocyclic radical; R represents hydrogen or a $C_1$-$C_{12}$ alkyl or cycloalkyl (saturated or unsaturated) or Ar as above; Im represents a 1-H-imidazol-1-yl group (unsubstituted or substituted); and Y represents a saturated or unsaturated $C_1$-$C_{12}$ alkyl or a group —Z—Ar in which Ar has the above meaning and —Z— is a saturated or unsaturated $C_1$-$C_{12}$ alkylene wherein each of the alkyl and the alkylene may have a carbon chain once or twice interrupted by or, in the case of the alkylene, terminated on its Ar-end by oxy, thio, sulfinyl or sulfonyl bridges, always with the proviso that at least one of Ar and Y is a heterocyclic radical. These compounds are wide-spectrum fungicides and bactericides, and the preferred compounds among them are hydrophilic.

10 Claims, No Drawings

HETEROCYCLIC IMIDAZOLYL VINYL ETHERS AND USE OF SAME AS FUNGICIDES OR BACTERICIDES

CROSS-REFERENCE TO EARLIER APPLICATIONS

This application is a continuation-in-part of both U.S. application Ser. No. 970,312 filed Dec. 18, 1978 and U.S. application Ser. No. 970,330 filed Dec. 18, 1978, now issued as U.S. Pat. Nos. 4,210,656 and 4,210,657, respectively.

DESCRIPTION

This invention concerns imidazolyl vinyl ethers of the general formula

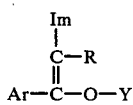

and their acid addition salts, wherein

Ar signifies (i) a saturated or unsaturated heterocyclic radical having one or two ring systems of preferably aromatic nature and further having up to four hetero atoms per radical, or (ii) phenyl or naphthyl, wherein the radicals both of (i) and (ii) may be unsubstituted or mono- or polysubstituted with substituents that are independently selected from the group consisting of halogeno, alkyl and cycloalkyl of up to 6 carbon atoms each, trifluoromethyl, alkoxy and alkylthio of from 1 to 6 carbon atoms in the alkyl portion of each, phenyl, benzyl, cyano, nitro and amino, Im signifies unsubstituted 1-H-imidazol-1-yl or substituted 1-H-imidazol-1-yl which has 1 to 3 substituents independently selected from the group consisting of halogeno, alkyl and an alkoxy of 1 to 4 carbon atoms, and not more than one nitro group, Y signifies (a) unbranched or branched aliphatic or cycloaliphatic hydrocarbyl of up to 12 carbon atoms which either is saturated or is unsaturated and contains one or more double and/or triple bonds, or (b) Ar as defined above, or (c) —Z—Ar wherein Ar is as defined above and Z is alkylene or alkylene having its carbon chain on the Ar-end terminated by and/or once or twice interrupted by a linkage selected from the group consisting of oxy, thio, sulfinyl or sulfonyl, or (d) an aliphatic hydrocarbyl as defined in (a) above wherein the carbon chain linked to the ether oxygen is once or twice interrupted by a linkage selected from the group consisting of oxy, thio, sulfinyl and sulfonyl, with the proviso that at least one of Ar and Y must be a heterocyclic radical as defined in Ar (i) above, and R signifies (i) unbranched or branched aliphatic or cycloaliphatic hydrocarbyl of up to 12 carbon atoms which is either saturated or contains one or more double and/or triple bonds, (ii) Ar as defined above, or (iii) hydrogen.

The invention further concerns the use of these imidazolyl vinyl ethers, as well as their addition salts as formed with acids that are acceptable for bactericidal and fungicidal use, as pesticides, i.e., fungicides and/or bactericides. They may be used for this purpose by themselves or in the form of compositions in admixture with an inert carrier and, if desired, with various other known auxiliary agents. They are particularly useful for controlling fungi and bacteria in industrial equipment.

Above-identified copending U.S. patent applications Ser. Nos. 970,312 and 970,330, the full text of both of which is incorporated herein by reference, disclose and claim certain imidazolyl vinyl ether compounds that are useful as fungicides or bactericides, especially in the medical, agricultural and horticultural fields, i.e., in fields involving an essentially organic or living substrate. However, such previously claimed compounds generally lack sufficient heterocyclic functionality to be hydrophilic in nature and therefore do not easily lend themselves for non-medical or non-agricultural use, such as for controlling fungi or bacteria in industrial equipment, i.e., on inorganic substrates or surfaces composed of metal, glass, etc.

Imidazol-1-yl derivatives are easily obtainable fungicides and bactericides of low toxicity with a wide spectrum of activity. However, resistances and partial resistances are frequently observed when they are used. The imidazolyl vinyl ethers corresponding to formula (I) shown above in many cases display surprisingly satisfactory activity where other imidazolyl derivatives bring about resistance. The presently disclosed imidazolyl vinyl ethers thus supplement, widen and intensify the spectrum of activity heretofore available in other compounds, and above all are capable of providing effective hydrophilic fungicides and bactericides that meet increasing industrial needs for this type of agent.

Of course, it will be understood that compounds of this invention may comprise a wide variety of substituents as indicated above by the definitions of Ar, Im, Y, and R and that these various substituents will tend to affect the chemical, physiological and physical properties of the basic structure to some degree, as may be desired. Obviously, if a hydrophilic nature of the product is a prime desideratum, the substituents will have to be suitably selected. More particularly, when a distinctly hydrophilic compound is wanted, hydrocarbon substituents and especially long-chain alkyl substituents will need to be avoided or in appropriate cases, their hydrophobic effect counter balanced by other substituents or moieties in the molecule that are hydrophilic, e.g., nitro, amino, halogeno, sulfonyl, etc. In any event, an acid salt of any such imidazolyl vinyl ether will tend to be more hydrophilic than the imidazolyl vinyl ether per se.

Compounds wherein at least one of the heterocyclic substituents or radicals Ar or Y is a five or six-membered ring containing a conjugation of unsaturated groups or atoms are preferred. Representative of these are the monovalent radicals, among the 5-membered heterocyclic systems, of furan, thiophene, pyrrole, coumarone, benzothiophene, indole, pyrazole, imidazole (glyoxalin), thiazole, oxazole, benzoxazole, triazole, tetrazole, carbazole, and, among the 6-membered heterocyclic systems, alpha- or gamma-pyrone, pyridine, pyridazine, pyrimidine, pyrazine, penthiophene, dioxane, chromone, flavone, and quinoline or isoquinoline.

As generally described in applicants' above-mentioned parent applications with reference to the compounds disclosed therein, the presently claimed imidazolyl vinyl ethers of the formula (I) are similarly prepared by reacting the corresponding 1-arylacylimidazole having the formula $$\text{Ar—C—CHR—Im} \quad \text{(III)}$$
$$\underset{O}{\|}$$

with a halide of the formula $$\text{Hal—Y} \quad \text{(IV)}$$

in the presence of NaH with initial cooling with ice and subsequent mild heating, and by working up the reaction mixture in the usual manner. Hal in formula (IV) signifies a halogen atom, e.g., chlorine, bromine or iodine, and Y has the meaning given above in connection with formula (I). The reaction is conducted with stirring in a solvent, preferably in hexamethylphosphoric acid triamide.

In a few cases the C-alkylation cannot be totally prevented when using the above-described manner of preparation. However, the ethanone derivatives of the general formula $$\text{Ar—CO—CRY—Im} \quad \text{(V)}$$

which are thus obtained as byproducts only become apparent in the chromatographic column separation after the less polar substances of the general formula (I) have been eluted, and thus are readily separable from the desired products.

Besides the above named sodium hydride, which is preferably added as a dispersion in white mineral oil, alkali metals, alkaline earth metals as well as their hydrides and alcoholates, lithium organic compounds, sodium amide or mono- or di-N- substituted sodium amides can be used as condensation agents.

The invention is further described by means of the following examples.

EXAMPLE 1

2-Thien-2-yl-2-(2-(4-chlorophenoxy)-ethoxy)-1-(imidazol-1-yl)-ethylene hydrochloride

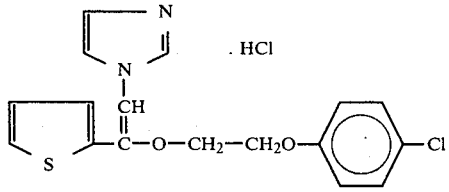

46.9 g (0.37 mol) 2-acetylthiophene are dissolved in a mixture of 130 ml ether and 65 ml dioxane. To the thus obtained mixture 59.2 g (0.37 mol) bromine is added dropwise in the course of 20 minutes while maintaining a temperature of 5°–10° C. within the reaction mixture. A solution of 120 g (1.76 mol) imidazole in 170 ml methanol then is added dropwise in the course of 30 minutes while maintaining the temperature of the mixture below 25° C. The mixture then is allowed to stand at room temperature for about 16 hours. After that time 400 ml H₂O is added and the volume of the liquid mixture is reduced under vacuum to about 250 ml. The residue of 250 ml liquid reaction mixture then is made up with water to a total volume of 1.5 l. The aqueous reaction mixture then is repeatedly extracted with chloroform. The combined chloroform extracts are dried with sodium sulfate and purified by filtration. The filtrate then is completely stripped of the solvent by evaporation under vacuum. The obtained residue is a dark oil which is taken up in 400 ml acetic acid ethyl ester. 20 ml of concentrated HNO₃ is added to the suspension thus obtained. The resulting crystalline precipitate is separated by filtration while applying reduced pressure. The residue is a light brown crystalline crude product which is further purified by re-crystallization from 100 ml ethanol in the presence of active carbon and final re-crystallization from 200 ml of a mixture (1:1) of ethanol and chloroform. This yields 17.8 g 1-imidazol-1-yl-2-thien-2-yl-ethane-2-one nitrate in the form of almost colorless crystals having a melting point of 110°–120° C.

7.7 g (30 mmol) of the obtained ethanone is dissolved in 50 ml hexamethylphosphoric acid triamide and mixed in increments with 4.0 g of a 50% dispersion of NaH in a highly refined white mineral oil at room temperature. When the reaction has subsided the mixture is heated 1 hour at 50° C. while stirring, and then is allowed to cool to room temperature again. After adding 7.1 g (30 mmol) 2-(4-chlorophenoxy)-ethylbromide the mixture is again heated 3 hours at 50° C. while stirring. The reaction mixture then is allowed to stand 16 hours at room temperature.

The reaction mixture then is poured into water and extracted with diethyl ether. The combined ether extracts are washed with water and dried with sodium sulfate. The solid material is separated by filtration, and the filtrate is evaporated under reduced pressure. The residue is a dark oil to which a solution of hydrogen chloride in ether is added. The precipitate thus obtained is thoroughly mixed and shaken with ether. After phase separation the ether is decanted, and the residue is mixed with ethyl acetate. The ether ethyl acetate treatment is repeated and then yields a crystalline mass which can be separated by suction filtration. The crystals thus obtained then are recrystallized from 20 ml isopropanol. The finally separated and purified vinylether hydrochloride end product has a melting point of 176°–177° C.

The corresponding nitrate is obtained by reacting the oily residue with concentrated nitric acid rather than with etheric hydrogen chloride solution.

The purity of the obtained substances is tested in an IR spectrum.

| Elemental analysis for C₁₇H₁₅ClN₂O₂S . HCl (mol. wt. 383.3): | | | | | |
|---|---|---|---|---|---|
| | C (%) | H (%) | N (%) | Cl (%) | S (%) |
| calc. | 53.27 | 4.21 | 7.31 | 18.50 | 8.36 |
| found | 52.95 | 4.20 | 7.48 | 18.72 | 8.63 |

EXAMPLE 2

2-(2,4-Dichlorophenyl)-2-(5-chloropyrid-2-yl-thio)-methoxy-1-(imidazol-1-yl)-ethylene nitrate

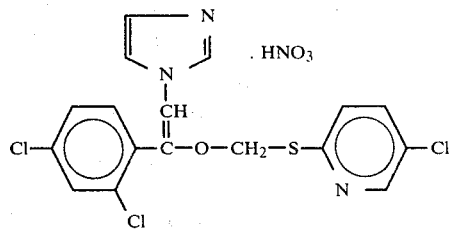

The compound prepared in this example is the same as the one described in Example 9 of parent application Ser. No. 970,312 filed Dec. 18, 1978, now U.S. Pat. No. 4,210,656.

2-mercapto-5-chloro-pyridine is prepared from 2,5-dichloropyridine according to A. Binz and C. Rath (Liebigs Ann. 487 (1931), 108). Using the method of U.S. Pat. No. 4,014,891, the 2-mercapto-5-chloro-pyridine is converted to 5-chloro-2-chloromethylthio-pyridine.

Further, a suspension of 16.43 g (64.4 mmol) 1-(2,4-dichlorophenacyl)-imidazole in 50 ml hexamethylphosphoric acid triamide is mixed in small increments with 3.09 g (64.4 mmol) of a 50% dispersion of NaH in a highly refined white mineral oil at a temperature in the range of 0°–5° C. When the reaction subsides, the reaction mixture is stirred 2 hours at room temperature and then stirred 2 additional hours at 60° C. After that the mixture is cooled down to 10° C. and slowly mixed dropwise with 12.5 g (64.4 mmol) of the above-obtained 5-chloro-2-chloromethylthio-pyridine, dissolved in hexamethylphosphoric acid triamide. The mixture then is stirred about 16 hours at room temperature, and further is stirred 2 hours at 60° C.

The reaction mixture is allowed to cool to room temperature and then poured into 1 l of water. The water phase is then three times agitated with 250 ml ethyl acetate, and the combined ethyl acetate extract fractions are dried with sodium sulfate. The combined and dried fractions are purified by filtration and completely stripped from the solvent under reduced pressure. The residue obtained is a dark brown oil which is purified in a chromatographic column charged with 650 g silica gel. The column is eluted with dichloromethane.

Eluate fractions nos. 2–6, each having a volume of 800 ml, are combined and evaporated. The obtained residue is a brownish oil which is dissolved in 30 ml ethyl acetate and precipitated in the form of the nitrate by adding concentrated nitric acid. The separated crude nitrate is recrystallized from 145 ml ethanol admixed with active carbon yielding 5.2 g of colorless, crystalline, pure 2-(2,4-dichlorophenyl)-2-(5-chloropyrid-2-yl-thio)-methoxy-1-(imidazol-1-yl) ethylene nitrate. This product melts at 165°–166° C. with decomposition.

| Elemental analysis for $C_{17}H_{12}Cl_3N_3OS \cdot HNO_3$ (mol. wt. 475.7): | | | |
| --- | --- | --- | --- |
| | C (%) | H (%) | N (%) |
| calc. | 42.92 | 2.75 | 11.78 |
| found | 42.64 | 2.36 | 11.61 |

The chemical structure and the purity of the thus obtained enol ether is checked and verified by IR spectra.

In the same manner as described in Example 2, the following compounds are prepared from the starting compounds indicated:

EXAMPLE 3

2-(2,4-Dichlorophenyl)-2-(2-(5-chloropyrid-2-yl-oxy)-ethoxy)-1-(imidazol-1-yl)-ethylene is prepared starting from 5-chloropyridine-2-ol.

EXAMPLE 4

2-(2,4-Dichlorophenyl)-2-(2-(5-chloropyrid-2-yl-thio)-ethoxy)-1-(imidazol-1-yl)-ethylene is prepared starting from 5-chloro-2-mercapto-pyridine

EXAMPLE 5

2-(2,4-Dichlorophenyl)-2-(2-(5-bromothien-2-yl-methoxy)-ethoxy)-1-(imidazol-1-yl)-ethylene is prepared starting from 5-bromo-thiophene-2-aldehyde, which is then reduced by means of NaH to the corresponding alcohol and reacted with 1-bromo-2-chloroethane to yield 5-bromo-2-(2-chloroethoxymethyl)-thiophene, which is then reacted with the corresponding 1-(2,4-dichlorophenacyl)-imidazole as in Example 2.

EXAMPLE 6

2-(4-Chlorophenyl)-2-(2-(5-chloropyrid-2-yl-oxy)-ethoxy)-1-(imidazol-1-yl)-ethylene is prepared starting from the respective 1-(4-chlorophenacyl)-imidazole.

Salts, especially the nitrates and hydrochlorides of said compounds, can be readily made by adding concentrated nitric acid and hydrochloric acid, respectively, to the corresponding non-purified base and thereby precipitating the salt from the mixture.

In the same manner as described in Example 1 the following compounds were made:

EXAMPLE 7

2-(Pyrid-2-yl)-2-(2-(4-chlorophenoxy)-ethoxy)-1-(imidazol-1-yl)-ethylene is prepared starting from 2-acetyl-pyridine.

EXAMPLE 8

2-Fur-2-yl-2-(2-(4-chlorophenoxy)-ethoxy)-1-(imidazol-1-yl)-ethylene is prepared starting from 2-furylmethylketone.

EXAMPLE 9

2-(1H-1-Methylindol-3-yl)-2-n-butoxy-1-(imidazol-1-yl)-ethylene is prepared starting from 3-acetylindole.

Similarly, as is obvious to a man skilled in the art from the above Examples 1 through 9, the following compounds are prepared in an analogous manner:

2-Thien-2-yl-2-(2-(5-bromothien-2-yl-methoxy)-ethoxy)-1-(imidazol-1-yl)-ethylene.

2-Quinol-2-yl-2-(2-(5-bromothien-2-yl-methoxy)-ethoxy)-1-(imidazol-1-yl)-ethylene.

1,2-Di-imidazol-1-yl-2-(2-(5-chloropyrid-2-yl-oxy)-ethoxy)-ethylene.

2-(1,2,4-Triazol-1-yl)-2-(2-(5-chloropyrid-2-yl-ethoxy)-ethoxy)-1-(imidazol-1-yl)-ethylene, and 2-(1,2,4-Triazol-3-yl)-2-(2-(5-chloropyrid-2-yl-oxy)-ethoxy-1-(imidazol-1-yl)-ethylene.

Tests

The compounds prepared according to Examples 1 and 2 are evaluated for their bactericidal and fungicidal activity. For determination of the minimum blocking concentration (MIC), the gradient plate method with gradients from zero to 100 μg/ml is resorted to. The compounds to be examined are used as solutions in 10% dimethylformamide. Reading of the results takes place three days after starting the test, and the resulting data are compared to the commercially available, well-known fungicide α-(2,4-dichlorophenyl)-β-imidazol-1-yl-ethyl-(4-chlorophenyl)-methylether nitrate, which is used as a control. The bacteria Staphylococcus aureus haemolyticus (St) and Streptococcus faecalis (Str) and the fungi Candida albicans (Ca), Trichophyton mentagrophytes (Tri) and Aspergillus niger (Asp) serve as test organisms.

The obtained test data for the compounds of Examples 1 and 2 are in each instance at least comparable and in some instances better than the data obtained for the control compound used as a point of reference. In contrast to the control compound, however, the compounds of Examples 1 and 2 of the invention were hydrophilic and thus could easily be applied to glass and steel plates by mere brushing and spraying of the diluted compounds on the substrate.

The active compounds can be applied to substrates in the form of dusts when diluted with powdered solid carriers such as clays, or in the form of aqueous dispersions or solutions, or they may be included in otherwise conventional soaps or synthetic detergent compositions used for washing walls or floors or tanks or other industrial equipment.

The invention is particularly pointed out and claimed in the appended claims.

What is claimed is:

1. An imidazolyl vinyl ether having the formula

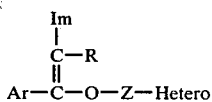

or an acid addition salt thereof acceptable for bactericidal or fungicidal use, wherein Ar is a radical selected from the group consisting of phenyl, naphthyl, 4-halo-phenyl and 2,4-dihalo-phenyl, R is either hydrogen, methyl, ethyl, propyl or butyl, Im signifies unsubstituted 1-H-imidazol-1-yl or substituted 1-H-imidazol-1-yl which has one to three substituents independently selected from the group consisting of halogeno, alkyl and alkoxy of one to four carbon atoms, and not more than one nitro group, Z is $C_1$–$C_{12}$ alkylene or $C_1$–$C_{12}$ alkylene having its carbon chain on the Hetero-end terminated by and/or once or twice interrupted by a linkage selected from the group consisting of oxy, thio, sulfinyl or sulfonyl, and Hetero is thienyl, pyridyl, furyl, pyrrolyl, imidazolyl, pyrazolyl, triazolyl, pyrimidinyl, pyridazinyl, benzothienyl, indolyl, benzofuryl, pyrazinyl, quinolyl or quinazolinyl, each of which is either unsubstituted or mono- or polysubstituted with substituents that are independently selected from the group consisting of halogeno, trifluoromethyl, alkyl, cycloalkyl, alkoxy and alkylthio of from one to six carbon atoms in the alkyl or cycloalkyl portion of each, phenyl, benzyl, cyano, nitro and amino.

2. An imidazolyl vinyl ether according to claim 1 wherein Hetero contains one or two halo substituents.

3. An imidazolyl vinyl ether according to claim 1 selected from the group consisting of 2-(2,4-dichlorophenyl)-2-(5-chloropyrid-2-yl-thio)-methoxy-1-(imidazol-1-yl)ethylene, 2-(2,4-dichlorophenyl)-2-(2-(5-chloropyrid-2-yl-oxy)-ethoxy)-1-(imidazol-1-yl)-ethylene, 2-(2,4-dichlorophenyl)-2-(2-(5-chloropyrid-2-yl-thio)-ethoxy)-1-(imidazol-1-yl)-ethylene, 2-(2,4-dichlorophenyl)-2-(2-(5-bromothien-2-yl-methoxy)-ethoxy)-1-(imidazol-1-yl)-ethylene, 2-(4-Chlorophenyl)-2-(2-(5-chloropyrid-2-yl-oxy)-ethoxy)-1-(imidazol-1-yl)-ethylene, and nitrate salts thereof.

4. 2-(2,4-Dichlorophenyl)-2-(5-chloropyrid-2-yl-thio)-methoxy-1-(imidazol-1-yl)ethylene nitrate.

5. A fungicidal composition comprising an effective amount of at least one of the compounds of claim 1 in admixture with an inert carrier.

6. A fungicidal composition comprising an effective amount of at least one of the compounds of claim 3 in admixture with an inert carrier.

7. A process for controlling fungi or bacteria which comprises applying to a substrate containing same an effective amount of a compound of claim 1.

8. A process according to claim 7 wherein said substrate comprises a surface composed essentially of metal or glass and said compound is hydrophilic.

9. A process for controlling fungi selected from the group consisting of *Candida albicans, Thichophyton mentagrophytes* or *Aspergillus niger* which comprises applying to said fungi a fungicidally effective amount of at least one compound of claim 3.

10. A process according to claim 9 wherein said compound is 2-(2,4-dichlorophehyl)-2-(5-chloropyrid-2-yl-thio)-methoxy-1-(imidazol-1-yl)-ethylene.

* * * * *